United States Patent [19] [11] 4,037,474
Kost [45] July 26, 1977

[54] REPRESENTATIVE SAMPLING DEVICE
[75] Inventor: Walter Robert Kost, Minneapolis, Minn.
[73] Assignee: General Mills, Inc., Minneapolis, Minn.
[21] Appl. No.: 655,924
[22] Filed: Feb. 6, 1976
[51] Int. Cl.² ........................................... G01N 1/02
[52] U.S. Cl. ................................. 73/421 R; 209/137
[58] Field of Search ............ 73/421 R, 421 A, 421 B; 209/136, 137, 138

[56] References Cited
U.S. PATENT DOCUMENTS

| 33,634 | 11/1861 | Bruckshaw et al. | 209/137 |
| 3,738,483 | 6/1973 | MacKenzie | 209/137 X |

Primary Examiner—Richard C. Queisser
Assistant Examiner—Joseph W. Roskos
Attorney, Agent, or Firm—Kenneth D. Ohm; G. O. Enockson

[57] ABSTRACT

A hopper into which loosened pieces of the paper collection are fed. A conveyor for transporting the loosened pieces of paper to a higher elevation. A fan for generating a stream of air to blow through the pieces of paper as they leave the conveyor at the higher elevation. A chamber into which the pieces of paper are gently floated by the stream of air generated by the fan. A vertical tube through which the pieces of paper can flutter downwardly due to the force of gravity. A divider separating the bottom of the vertical tube into a number of parts so that the pieces of paper which flutter down the tube can be separated into desired proportions.

10 Claims, 3 Drawing Figures

REPRESENTATIVE SAMPLING DEVICE

The present invention relates to an apparatus for separating out a representative sample from a collection of various sizes, shapes and weights of pieces of paper and/or cardboard. More particularly, it pertains to an apparatus for selecting such a representative sample from which statistical data concerning the entire make-up of such collection can be derived.

One object of the present invention is to provide an apparatus for separating out a fraction from a collection of various sizes, shapes and weights of pieces of paper and/or cardboard (e.g., coupons) from which statistical data concerning the entire make-up of such collection of papers can be derived.

Other objects and advantages of the invention will be apparent from the following description in which certain preferred embodiments of the invention are disclosed.

Figure 1:
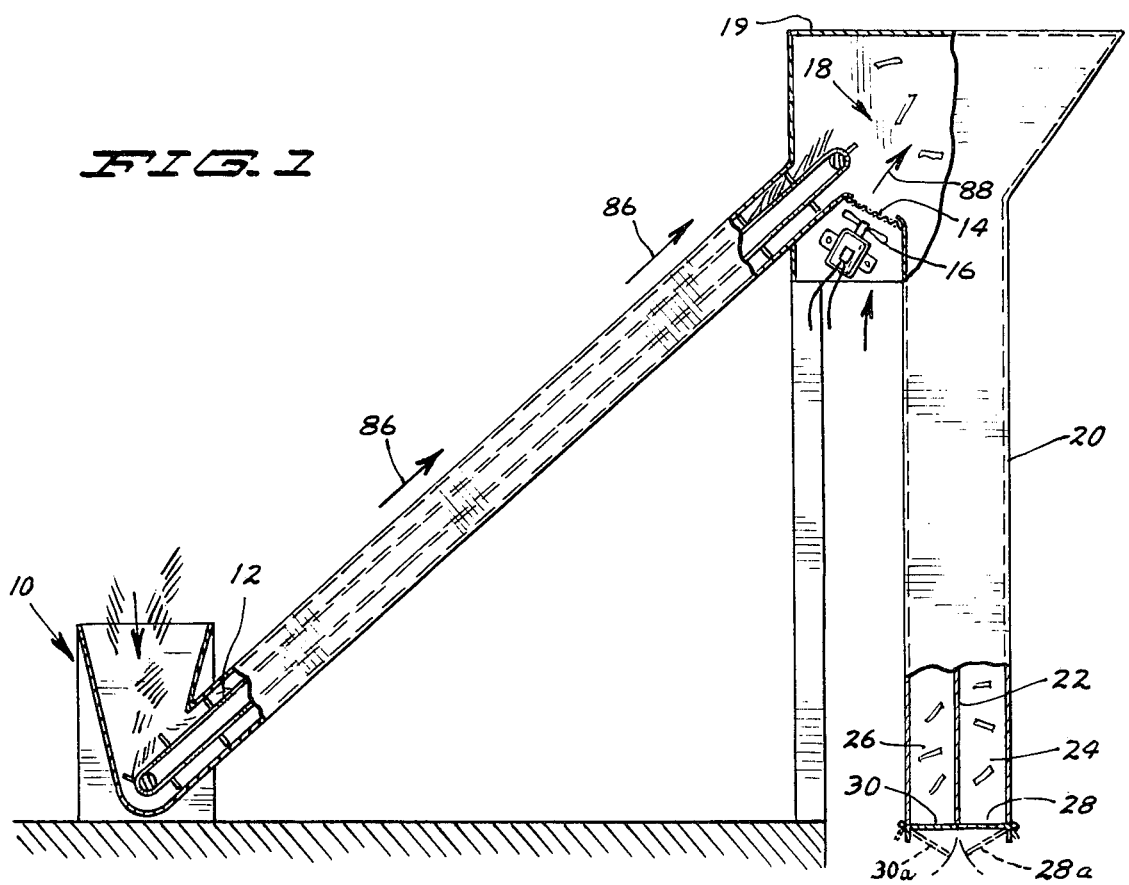
Figure 2:
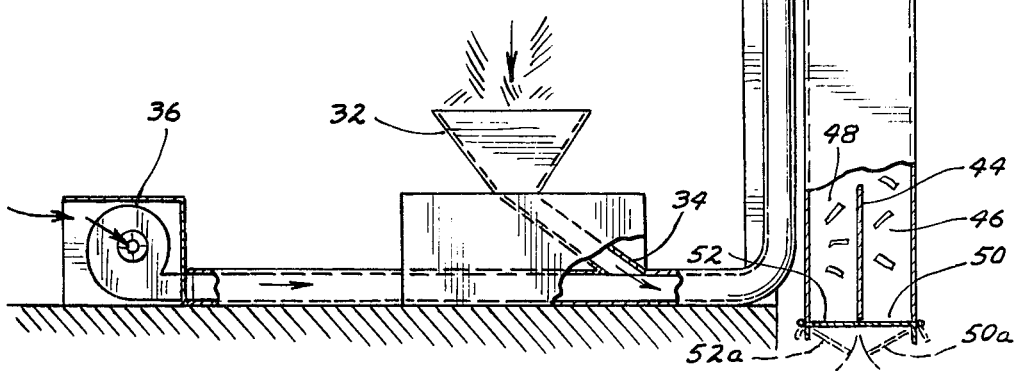
Figure 3:
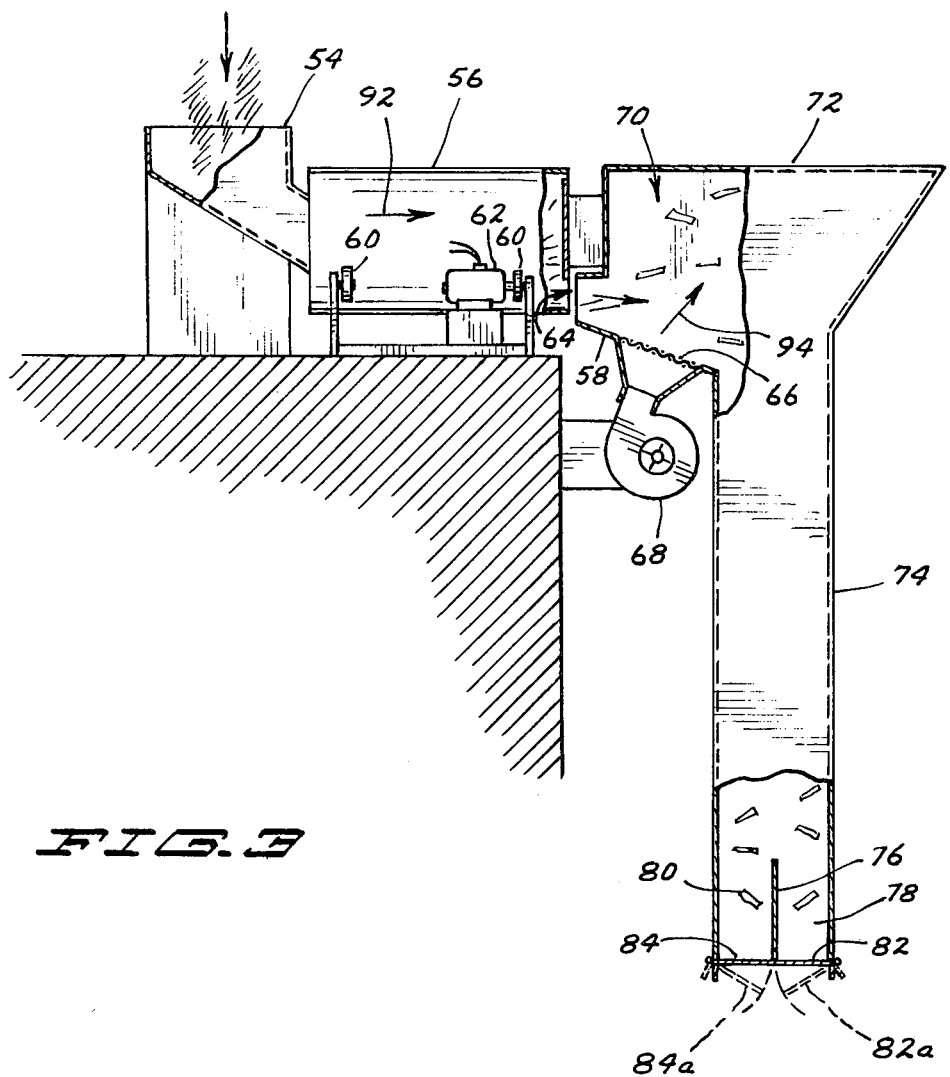

In the drawings which form a part of this application,

FIG. 1 is a perspective view illustrating one form of the present invention, and FIG. 2 is a perspective view illustrating another form of the present invention, and FIG. 3 is a perspective view illustrating a further form of the present invention.

Referring now to FIG. 1, one embodiment of a representative sampling apparatus of the present invention comprises a hopper 10 positioned above one end of a belt conveyor 12. The other end of the belt conveyor 12 is located adjacent a screen 14.

A fan 16 is positioned directly below the screen 14 so that the stream of air generated by the fan 16 blows through the screen 14.

A chamber 18 is positioned above and off to the side of the screen 14. The chamber 18 has a vented cover 19. A vertical tube 20 is attached to the lower portion of the chamber 18. The lower portion of the tube 20 is provided with a divider 22. The divider 22 separates the bottom of the tube 20 into two equal parts 24 and 26. The bottom of the parts 24 and 26 are provided with movable hinged doors 28 and 30, respectively. The doors 28 and 30 are shown by the solid lines in their closed positions and dotted lines indicated by numerals 28a and 30a in their open positions.

Referring now to FIG. 2, there is shown an alternate form of the present invention. In this alternate form the hopper 10, the conveyor 12, the screen 14 and the fan 16 are replaced with a hopper 32, a chute 34, a motor driven fan 36, and a forced air chute 38.

A chamber 40 is positioned above the air chute 38. The chamber 40 has a vented cover 41. A vertical tube 42 is attached to the lower portion of the chamber 40. The lower portion of the tube 42 is provided with a divider 44.

The divider 44 separates the bottom of the tube 42 into two equal parts 46 and 48. The bottom of the parts 46 and 48 are provided with movable hinged doors 50 and 52, respectively. The doors 50 and 52 are shown in their closed positions and the dotted lines indicated by numerals 50a and 52a show their respective open positions. In this alternate form of FIG. 2 a sufficient force of air is generated by the fan 36 to elevate the collection of paper vertically to the chamber 40 when fed in through the hopper 32 and down the chute 34. The cover 41 of the chamber 40 is vented to release the force of air which permits the collection of paper to slide down the sides of the chamber 40 to the vertical tube 42 where the pieces flutter downwardly due to the force of gravity.

Referring now to FIG. 3, there is shown another alternate form of the present invention. In this alternate form the hopper 10 and conveyor 12 of FIG. 1 are replaced with a hopper 54, a rotating drum 56 having rod protrusions on the interior thereof and an inclined slide 58. The drum is mounted on rollers such as 60 and rotated by a motor 62 as is well known in the art. One end of the slide 58 is located adjacent the outlet 64 of the drum 56 and the other end of the slide 58 is located adjacent a screen 66.

A fan 68 is positioned directly below the screen 66 so that the stream of air generated by the fan 68 blows through the screen 66.

A chamber 70 is positioned above and off to the side of the screen 66. The chamber 70 has a vented cover 72. A vertical tube 74 is attached to the lower portion of the chamber 72. The lower portion of the tube 74 is provided with a divider 76. The divider 76 separates the bottom of the tube 74 into two equal parts 78 and 80. The bottom of the parts 78 and 80 are provided with movable hinged doors 82 and 84, respectively. The doors 82 and 84 are shown in their closed positions and the dotted lines indicated by numerals 82a and 84a show their respective open positions.

The tubes 20, 42, and 74 can be constructed of ¼ inch screen enclosed with polyethylene to prevent outside air currents from influencing the fall of the pieces of paper as they flutter downwardly. The tubes could also be constructed of sheet metal. In the apparatus built like that shown in FIG. 1 the tube was fourteen feet high and thirty inches in diameter. The dividers 22, 44 and 76 can be made to separate the bottom of the tubes 20, 42 and 74, respectively, into more than two equal parts.

In the operation of the apparatus shown in FIG. 1, the collection of pieces of paper are freed from any devices that may hold one piece to another, such as paper clips, rubber binders, adhesive tape, etc. and shaken into the hopper 10. As these pieces of paper fall out of the hopper onto the conveyor 12 they are moved upwardly by the conveyor 12 in the direction of the arrow 86 where at the upper part of the conveyor 12 they are deposited on the screen 14.

The fan 16 generates a stream of air which blows in the direction of arrow 88. The stream of air from the fan 16 separates the pieces of paper which might be held together by static electricity and gently tosses the pieces of paper into the chamber 18. This chamber is vented at the top to allow the air generated by the fan 16 to escape upwardly.

After leaving the stream of air generated by the fan 16, the pieces of paper which have been gently tossed into the chamber 18, gently flutter downwardly through the tube 20 due to the force of gravity. At the base of the tube 20 the pieces of paper which flutter down the tube 20 are separated into two equal fractions by the divider 22.

In the operation of the apparatus shown in FIG. 2, the collection of pieces of paper are freed from any device that may hold one piece to another, such as paper clips, rubber binders, adhesive tape, etc., and shaken into the hopper 32. As these pieces of paper fall out of the hopper 32 into the chute 34 they are moved upwardly through the forced air chute 38 in the direction of the arrow 90 by the air stream produced by the fan 36. As these pieces of paper leave the forced air chute 38 in the direction of the arrow 91 they are gently tossed into the chamber 40. The stream of air from the fan 36 separates the pieces of paper which may be held together by static electricity. The chamber 40 is vented at the top to allow the air entering therefrom from the fan 36 to escape upwardly.

After leaving the stream of air generated by the fan 36, the pieces of paper gently flutter downwardly through the tube 42 due to the force of gravity. At the base of the tube 42 the pieces of paper which flutter down the tube 42 are separated into two equal fractions by the divider 44.

In the operation of the apparatus shown in FIG. 3, the collection of pieces of paper are freed from any devices that may hold one piece to another, such as paper clips, rubber binders, adhesive tape, etc. and shaken into the hopper 54. As these pieces of paper fall out of the hopper 54 into the rotating drum 56 they are moved through the drum 56 in the direction of arrow 92 by the rod protrusions on the interior thereof and the fact that the drum is slightly inclined and rotates. These loosened pieces of paper pour out of the drum opening 64 onto the inclined slide 58. At the end of the slide 58 the pieces of paper are deposited on the screen 66. The fan 68 generates a stream of air which blows in the direction of arrow 94. The stream of air from the fan 68 separates the pieces of paper which might be held together by static electricity and gently tosses the pieces of paper into the chamber 70. This chamber is vented at the top to allow the air generated by the fan 68 to escape upwardly.

After leaving the stream of air generated by the fan 68, the pieces of paper gently flutter downwardly through the tube 74 due to the force of gravity. At the base of the tube 74 the pieces of paper which flutter down the tube 74 are separated into two equal fractions by the divider 76.

The primary function of the hopper 10 and the conveyor 12 of FIG. 1, the hopper 32, the slide 34, the fan 36 and the chute 38 of FIG. 2, and the hopper 54, the rotating drum 56 and the inclined slide 58 of FIG. 3 is to convey the pieces of paper in an even flow into the chambers 18, 40 and 74, respectively.

Some alternatives for the hopper 10 and the conveyor 12 of FIG. 1, the hopper 32, the slide 34, the fan 36 and the chute 38 of FIG. 2, and the hopper 54, the rotating drum 56 and inclined slide 58 of FIG. 3 are (1) a conveyor which could empty the pieces of paper into a flailer before the pieces of paper go into a chamber like 18, and (2) a rotating drum having an internal screw conveyor to move the pieces of paper from the end at which they are dumped into the drum to the end where they fall out either on a screen like 14 or directly into a chamber like 18.

In view of the principles set forth herein, I have shown some of the ways of carrying out the present invention and some of the equivalents which are suggested by these disclosures.

Now, therefore, I claim:

1. An apparatus for separating out a representative sample from a collection of various pieces of paper comprising a chamber having an upper and a lower portion, means for conveying the pieces of paper in an even flow into said chamber, means for generating a stream of air to blow through and gently toss the pieces of paper as they enter into said chamber, an elongated tube means adjacent the lower portion of said chamber through which the pieces of paper can free fall due to gravity after said pieces leave the said chamber, the sides of said tube being free of substantial inward convergence from its end adjacent the lower portion of said chamber to the lower portion of said tube to prevent the sliding of the pieces of paper down the sides of said tube which sliding would provide a separating out of such pieces different in make-up from that provided by the free fall of said pieces, and means associated with the lower portion of said elongated tube to divide the pieces of paper into desired proportions.

2. An apparatus for separating out a representative sample from a collection of various pieces of paper as called for in claim 1 wherein the means for conveying the pieces of paper includes a belt conveyor.

3. An apparatus for separating out a representative sample from a collection of various pieces of paper as called for in claim 1 wherein the means for conveying the pieces of paper includes a belt conveyor and a hopper adjacent said belt conveyor for directing the flow of the pieces of paper onto said belt conveyor.

4. An apparatus for separating out a representative sample from a collection of various pieces of paper as called for in claim 1 wherein the means for generating the stream of air includes a screen over which the pieces of paper pass after they enter said chamber and a fan which blows the stream of air through said screen.

5. An apparatus for separating out a representative sample from a collection of various pieces of paper as called for in claim 1 wherein the means for conveying the pieces of paper includes a forced air chute and the means for generating the stream of air produces a stream of air to blow through said forced air chute.

6. An apparatus for separating out a representative sample from a collection of various pieces of paper as called for in claim 5 wherein the means for conveying the pieces of paper includes an inclined chute connected to said forced air chute and a hopper associated with said inclined chute adjacent said inclined chute for directing the flow of the pieces of paper into said inclined chute.

7. An apparatus for separating out a representative sample from a collection of various pieces of paper as called for in claim 1 wherein said means for conveying the pieces of paper includes a rotating drum having an inlet and an outlet and an inclined slide adjacent the outlet of said drum.

8. An apparatus for separating out a representative sample from a collection of various pieces of paper as called for in claim 7 wherein said means for conveying the pieces of paper includes a hopper adjacent the inlet of said rotating drum for directing the flow of the pieces of paper into said drum.

9. An apparatus for separating out a representative sample from a collection of various pieces of paper as called for in claim 8 wherein the means for generating the stream of air includes a screen over which the pieces of paper pass after they leave said inclined slide and a fan which blows the stream of air through said screen.

10. An apparatus for separating out a representative sample from a collection of various pieces of paper as called for in claim 1 wherein the upper portion of said chamber is vented and said elongated tube is constructed to prevent air current from outside said tube from influencing the free fall of the pieces of paper.

* * * * *